and al. | | |

United States Patent [19]

Knöfel et al.

[11] 4,231,952
[45] Nov. 4, 1980

[54] PROCESS FOR THE PRODUCTION OF MONOISOCYANATE

[75] Inventors: Hartmut Knöfel, Odenthal-Erberich; Klaus König, Leverkusen, both of Fed. Rep. of Germany

[73] Assignee: Bayer Aktiengesellschaft, Leverkusen, Fed. Rep. of Germany

[21] Appl. No.: 827,913

[22] Filed: Aug. 26, 1977

[30] Foreign Application Priority Data

Sep. 4, 1976 [DE] Fed. Rep. of Germany ....... 2639931

[51] Int. Cl.³ ........................................... C07C 118/00
[52] U.S. Cl. .......................... 260/453 P; 260/453 PH
[58] Field of Search ....................... 260/453 PH, 453 P

[56] References Cited

U.S. PATENT DOCUMENTS

| | | | |
|---|---|---|---|
| 3,440,268 | 4/1969 | Stamm | 260/453 P |
| 3,644,461 | 2/1972 | Hennells | 260/453 P |
| 3,694,323 | 9/1972 | Cooper et al. | 260/453 SP |
| 3,969,389 | 7/1976 | Urbach et al. | 260/453 P |
| 4,069,238 | 1/1978 | Zanker | 260/453 P |

*Primary Examiner*—Dolph H. Torrence
*Attorney, Agent, or Firm*—Gene Harsh; Joseph C. Gil; R. Brent Olson

[57] ABSTRACT

This invention relates to an improved process for the production of aliphatic relatively low boiling monoisocyanates from the corresponding carbamic acid chlorides, comprising adding an at least equivalent quantity, based on the hydrogen chloride bound in the carbamic acid chloride, of a relatively high boiling organic monoisocyanate or polyisocyanate whose boiling point is higher than the boiling point of the relatively low boiling monoisocyanate to be produced, to the carbamic acid chloride, optionally dissolved in inert organic solvents and then distilling off the relatively low boiling monoisocyanate by heating and/or applying a vacuum, or by means of an inert gas stream.

11 Claims, No Drawings

PROCESS FOR THE PRODUCTION OF MONOISOCYANATE

BACKGROUND OF THE INVENTION

It is known that isocyanates can be prepared by reacting amines with phosgene. This reaction proceeds via the carbamic acid chloride, which decomposes at elevated temperatures into the corresponding isocyanate and hydrogen chloride. If the boiling point of the isocyanate to be prepared is distinctly higher than the decomposition temperature of the carbamic acid chloride, the hydrogen chloride liberated by the decomposition reaction can easily be removed from the reaction, especially if an inert organic solvent is used. If, however, the decomposition temperature of the carbamic acid chloride is close to the boiling point of the isocyanate or above it, the isocyanate enters the vapor phase above the reaction mixture and recombines with the hydrogen chloride to reform carbamic acid chloride. Decomposition is therefore incomplete in such cases and the isocyanate is obtained in only low yield and is contaminated with carbamic acid chloride.

These conditions apply to aliphatic monoisocyanates in which the aliphatic groups contain from 1 to 4 carbon atoms, the greatest difficulties being encountered in the preparation of methyl isocyanate.

Several processes intended to overcome these difficulties have been described in the patent literature. A major proportion of these processes involve the decomposition of carbamic acid chlorides with the use of hydrogen chloride acceptors.

Thus, for example, it is known to prepare isocyanates from carbamic acid chlorides in the presence of organic bases, e.g. tertiary amines, or carboxylic acid dialkylamides as described in German Offenlegungsschrift No. 1,593,554 or tetraalkyl ureas as described in U.S. Pat. No. 3,644,461 in organic solvents. The use of water as described in German Auslegeschrift No. 2,156,761 and of aqueous solutions or suspensions of inorganic bases as described in British Pat. No. 1,208,862 for the absorption of hydrogen chloride has also been described. Olefines have also been mentioned as hydrogen chloride acceptors in German Offenlegungsschrift No. 2,210,285.

All these processes have the serious disadvantage of giving rise to by-products, in the form of corrosive organic or inorganic salts or alkyl chlorides, which must either be removed by expensive methods or contaminate the surroundings. Moreover, the use of organic bases involves the risk of side reactions leading to dimers and trimers. In the presence of water, a considerable proportion of the carbamic acid chloride is hydrolyzed to the amine hydrochloride so that satisfactory yields can be obtained only in the case of the comparatively unreactive tertiary butyl isocyanate.

The preparation of low boiling aliphatic monoisocyanates by thermal decomposition of carbamic acid chlorides in organic solvents by special technical procedures is also known.

According to German Auslegeschrift No. 1,193,034, thermal decomposition of carbamic acid chloride is carried out in a reactor equipped with a reflux condenser and separating column. Hydrogen chloride escapes through the reflux condenser while the isocyanate, carbamic acid chloride and solvent are held back. The isocyanate formed in the reaction enters the column and can be removed at the head of the column. Most of the isocyanate is returned by means of a reflux divider so that the hydrogen chloride ascending the column is completely absorbed and returns to the reactor in the form of carbamic acid chloride.

When this process is carried out continuously, solution depleted of carbamic acid chloride is continuously removed from the reactor to be enriched with carbamic acid chloride in another apparatus and then returned to the reactor.

Variations of this process have been described in German Offenlegungsschriften Nos. 2,411,441; 2,411,442 and 2,422,211. These variations are based on the same principle as described above and differ only in the apparatus used.

Although the processes mentioned above make it possible for low boiling aliphatic monoisocyanates to be produced by thermal decomposition of carbamic acid chlorides, they have the following disadvantages:

1. The removal of hydrogen chloride requires reflux condensers with large cooling surfaces, which must be operated at high energy cost with a large amount of cooling fluid so that the isocyanate and carbamic acid chloride will be retained quantitatively.

2. Removal of isocyanate free from carbamic acid chloride by distillation from the reaction mixture requires highly efficient fractionating columns and adjustment of the reaction to a high reflux ratio.

3. Satisfactory results can only be obtained if relatively dilute carbamic acid chloride solutions are used (1 to 30%).

4. In a continuous process (which is the only kind suitable for large-scale commercial production), the reaction solution must be repeatedly recirculated.

Necessarily the reactants (isocyanate, carbamic acid chloride and solvent) must be repeatedly evaporated, condensed or cooled and reheated during the process, which entails high energy consumption. The use of dilute solutions and the necessity for repeated circulation result in a long dwelling time and hence low volume/time yields. The long dwelling time involves the risk of reduction in yield due to trimerization of the monoisocyanate. The process requires elaborate measuring and control techniques. This, together with the low volume/time yields and the necessity of using highly efficient fractionating columns result in high investment costs for commercial production.

DESCRIPTION OF THE INVENTION

It has now surprisingly been found that low-boiling aliphatic monoisocyanates may be produced in high yields from the corresponding carbamic acid chlorides without any of the disadvantages referred to above, by adding an equivalent or excess quantity of a relatively high boiling monoisocyanate or polyisocyanate to the carbamic acid chlorides, optionally dissolved in inert organic solvents, and distilling off the low-boiling monoisocyanate from the mixture, optionally together with the solvent, at moderately elevated temperature and/or in vacuo or removing the low boiling monoisocyanate using an inert gas stream. It is surprisingly possible by this process to isolate the low-boiling monoisocyanate under mild conditions in highly pure form and in a high volume-time yield. The problems caused by the elimination of hydrogen chloride and its recombination with the isocyanate to form the carbamic acid chloride in the gas zone will only occur to a slight extent. Following separation of the low-boiling isocyanate, the carbamic acid chloride of the relatively high boiling isocyanate is left behind. It may be thermally dissociated without difficulty into hydrogen chloride and isocyanate by conventional methods for the production of relatively high boiling isocyanates. The relatively high boiling isocyanate is recovered and may be re-used.

It had not been expected on the basis of the prior art that the hydrogen chloride would be transferred from the low-boiling isocyanate to the relatively high boiling isocyanate under conditions where the dissociation of carbamic acid chlorides into hydrogen chloride and isocyanate is barely in evidence. In addition, the transfer reaction surprisingly takes place at such a high velocity that the low-boiling isocyanate may be quickly removed from the equilibrium.

Accordingly, the present invention relates to a process for the production of monoisocyanates corresponding to the following general formula:

R—NCO wherein R represents an optionally olefinically unsaturated, optionally chlorine-substituted aliphatic hydrocarbon radical having from 1 to 5 carbon atoms; from the corresponding carbamic acid chlorides corrsponding to the following general formula:

R—NH—COCl wherein an at least equivalent quantity, based on the hydrogen chloride bound in the carbamic acid chloride, of an organic monoisocyanate or polyisocyanate having a boiling point above the boiling point of the monoisocyanate to be produced, is added to the carbamic acid chlorides, optionally dissolved in inert organic solvents, and the monoisocyanate is distilled off from the thus-obtained mixture, optionally together with the solvent, by heating and/or by applying a vacuum or is removed, optionally together with the solvent, by means of an inert gas stream.

Starting compounds for the process according to the present invention are carbamic acid chlorides having the following general formula:

R—NH—CO—Cl in which R represents an optionally olefinically unsaturated C$_1$–C$_5$ aliphatic hydrocarbon radical optionally substituted by chlorine atoms.

Examples of carbamic acid chlorides corresponding to the above general formula are methyl, ethyl, isopropyl, allyl, m-amyl or 2-chloroethyl carbamic acid chloride. Methyl, ethyl or isopropyl carbamic acid chloride is preferably used in the process according to the present invention, methyl carbamic acid chloride being particularly preferred. The carbamic acid chlorides may also be used in admixture with the corresponding isocyanates in the process according to the present invention. Such mixtures are formed, for example, by the partial thermal elimination of hydrogen chloride from carbamic acid chlorides.

The carbamic acid chlorides may be prepared by reacting the corresponding amines with phosgene in known manner.

To carry out the process according to the present invention, an organic isocyanate having a higher boiling point than the monoisocyanate to be produced is added to the carbamic acid chlorides. The relatively high boiling isocyanate preferably has a boiling point at least 100° C. above the boiling point of the monoisocyanate to be produced. The relatively high boiling isocyanate is used in at least equivalent quantities, based on the hydrogen chloride bound in the carbamic acid chloride. In general, the quantitative ratios are selected in such a way that from 1 to 10 mols of isocyanate groups in the relatively high boiling isocyanate are present per mol of carbamic acid chloride.

Suitable relatively high boiling isocyanates are, in particular, aliphatic and aromatic monoisocyanates or polyisocyanates, such as n-hexylisocyanate, cyclohexyl isocyanate, ω-chlorohexamethylene isocyanate, 2-ethyl hexylisocyanate, n-octyl isocyanate, dodecyl-isocyanate, stearylisocyanate, 1,4-tetramethylene diisocyanate, 1,6-hexamethylene diisocyanate, 1,12-dodecane diisocyanate, trimethyl hexamethylene diisocyanate, cyclohexane 1,3-diisocyanate, cyclohexane-1,4-diisocyanate, 1-isocyanato-3,3,5-trimethyl-5-isocyanato methyl cyclohexane, 2,4-hexahydrotolylene diisocyanate, 2,6-hexahydrotolylene diisocyanate, dicyclohexylmethane-4,4'-and/or 2,4'-diisocyanate and homologues methyl-substituted in the ortho-position to the isocyanate groups, xylylene diisocyanate, benzyl isocyanate, tolylene-2,4'- and 2,6'-diisocyanate and isomer mixtures thereof, 4,4'- and 2,4'-diphenyl methane diisocyanate and mixtures thereof, mixtures obtained by phosgenating aniline-formaldehyde condensates, and naphthylene 1,5-diisocyanate. It is preferred to use aliphatic monoisocyanates or polyisocyanates whose boiling points are at least 100° C. above those of the particular low boiling isocyanates to be produced in accordance with the present invention. Isocyanates having a relatively high isocyanate content, such as tetramethylene diisocyanate, hexamethylene diisocyanate and 1-isocyanato-3,3,5-trimethyl-5-isocyanato methyl cyclohexane, are particularly preferred.

Solvents which may optionally be used include, for example, aliphatic hydrocarbons, such as pentane, hexane, heptane, octane and cyclohexane; halogenated aliphatic hydrocarbons, such as methylene chloride, chloroform, carbon tetrachloride, n-propyl chloride, n-butyl chloride and isomers thereof, amyl chloride, cyclohexyl chloride, ethylidene chloride, dichlorethylene, ethylene chloride, dichloropropane, dichlorobutane, isopropyl bromide, n-propyl bromide, butyl bromide, ethyl iodide, propyl iodide and fluorinated or partly fluorinated compounds; aromatic and substituted aromatic hydrocarbons, such as benzene, toluene, xylene, ethylbenzene, chlorobenzene, dischlorobenzene, fluorobenzene, difluorobenzene, nitrobenzene, aromatic ethers; naphthalene derivatives, such as chloronaphthalene; ketones such as acetone, methyl ethyl ketone, diethyl ketone, acetophenone; esters, such as formic acid ethyl ester, acetic acid alkyl esters, propionic acid esters, phthalic acid esters and other high boiling esters; and other organic compounds, such as carbon disulphide, methyl-tert-butyl ester, ethyl propyl ether, tetrahydrofuran and acetonitrile. It is, of course, also possible to use mixtures of the above-mentioned solvents. Chlorobenzene, o-dichlorobenze and ethylene chloride are preferably used. The preferred solvents generally have a boiling point above the boiling point of the monoisocyanate to be produced, but are still readily volatile enough to be distilled together with the monoisocyanate product in the course of the process according to the present invention.

In the process according to the present invention, the low boiling isocyanates may be separated off with the assistance of inert carrier gases. Such gases include nitrogen, carbon dioxide, sulphur dioxide, helium, argon, hydrogen, air, methane, ethane, ethylene, propane, propene, butanes, butenes, methyl chloride and dichlorodifluoromethane.

The process according to the present invention is generally carried out as follows: The solution of the carbamic acid chloride or of a carbamic acid chloride/isocyanate mixture is mixed at room temperature in a suitable reaction vessel with an equivalent or excess quantity of the preferably aliphatic relatively high boiling isocyanate. At a sump temperature of from about −20° to about +100° C., preferably from about 0° to about 50° C., the low boiling isocyanate is distilled off under a pressure of from about 5 to about 760 Torr, preferably under a pressure of from about 10 to about 200 Torr, and condensed in a cooled receiver. The pressure is preferably selected in such a way that the solvent used, which boils at a distinctly higher temperature than the low boiling isocyanate, but below 150° C. (under normal pressure), distills at a temperature in the range indicated, thereby facilitating separation of the low boiling isocyanate. Isocyanate and solvent are separated from one another in a subsequent distillation stage.

In another advantageous embodiment of the process according to the present invention, the low boiling isocyanate is removed from the reaction mixture at a temperature below its boiling point by means of a stream of an inert carrier gas such as i.e. air or nitrogen and is isolated from the gas stream by freezing out as exemplified in examples 2 and 3. In order to avoid losses and to minimize the consumption of cooling energy, the gas stream is advantageously circulated. The solvent may, of course, also be at least partly removed together with the isocyanate, followed by separation of the monoisocyanate from the solvent by distillation. Basically, it is also possible not to use a solvent, although the use of such a solvent is preferred.

The process according to the present invention is particularly suitable for continuous operation, in which case several reaction vessels arranged one behind the other in the form of a cascade are used so that the effect according to the present invention may be enhanced in stages by repeated adjustment of the equilibrium.

The carbamic acid chloride or the above-mentioned mixture of carbamic acid chloride and the corresponding monoisocyanate are continuously delivered to the last vessel of the cascade. On completion of the reaction, it is transferred, having a reduced content of acid chloride and a correspondingly increased content of low boiling isocyanate, either by distillation or by means of a carrier gas to the preceding vessel of the cascade where the operation is repeated until the pure isocyanate is continuously removed from the first vessel of the cascade either by distillation or by means of a stream of an inert carrier gas. The relatively high boiling isocyanate is passed through the cascade in the opposite direction as liquid phase on the overflow principle, as a result of which it gradually becomes charged with HCl by equilibrium adjustment and is correspondingly converted into its carbamic acid chloride. After leaving the last vessel of the cascade, the carbamic acid chloride is conventionally regenerated into the relatively high boiling starting isocyanate in a separate part of the installation by boiling out hydrogen chloride and is recycled to the first vessel of the cascade. It is of advantage to continuously distill part of the relatively high boiling isocyanate in a side-stream before it is recycled to the cascade in order to remove high boiling or solid secondary products from the system.

In other respects, however, the construction of the apparatus used for the process according to the present invention is not significant to the practicability of the process according to the present invention. It is possible to use the apparatus normally employed in chemical engineering for corresponding reactions and process stages.

In the particular embodiment of the process according to the present invention where an inert carrier gas is used for removing the low boiling isocyanate, it is of advantage to use bubble tray columns or bubble columns instead of a cascade of vessels for this stage of the process by virtue of their greater effectiveness.

The monoisocyanates obtained in accordance with the present invention are valuable starting compounds for the production of pharmaceuticals and plant protection agents.

EXAMPLES

EXAMPLE 1

In a flask equipped with a stirrer and dephlegmator, 374 g (4.0 mol) of the carbamic acid chloride (CSC) of methyl isocyanate (MIC) are added to 55 g (2.5 mols) of 1-isocyanato-3,3,5-trimethyl-5-isocyanato cyclohexane (IPDI) in 700 ml of chlorobenzene. After a vacuum of from 20 to 30 Torr has been applied, the sump temperature in the flask is gradually increased to 40° C. under a constant vacuum. 802 g of distillate are condensed in a cold trap over a period of 2.5 hours. The distillate consists of:

211 g (3.7 mols) of MIC,
14 g (0.15 mols) of CSC and
577 g of chlorobenzene.

The sump left in the reaction flask is kept boiling under reflux at normal pressure. The quantity of hydrogen chloride gas which escapes is collected in a receiver containing aqueous sodium hydroxide and is analytically determined (131.5 g=3.6 mols). The contents of the flask left after the elimination of hydrogen chloride are finally distilled. 191 g of chlorobenzene and 524 g (2.36 mols) of IPDI are recovered in this way.

EXAMPLE 2

In a flask equipped with a stirrer and dephlegmator, 187 g (2.0 mols) of the carbamic acid chloride (CSC) of methyl isocyanate (MIC) are mixed while stirring with 336 g (2.0 mols) of hexamethylene diisocyanate and 200 g of chlorobenzene. At a temperature of the flask contents of 40° C., gradully rising to a maximum of 60° C., an air stream of about 200 liters/h is continuously passed through the reaction mixture at normal pressure by means of a submerged frit. The condensate (141 g) which accumulates in the condensor of the dephlegmator over a period of 2 hours at −30° C. is collected in the cooled distillation receiver and has the following composition:

81.1 g of MIC
4.2 g of CSC
55 g of chlorobenzene.

The carrier gas stream is continuously recirculated. The distillation residue (approximately 575 g) is worked up in the same way as in Example 1. The condensate is rereacted with 168 g (1.0 mol) of hexamethylene diisocyanate. An air stream of about 200 liters/h is again passed continuously through the mixture under normal pressure, the temperature of the mixture not exceeding 40° C. The condensate (74.5 g) which accumulates in the condensor over a period of 1 hour at −30° C. has the following composition:

59.4 g of MIC
<0.1 g of CSC
approx. 15 g of chlorobenzene.

EXAMPLE 3

187 g (2.0 mols) of the carbamic acid chloride (CSC) of methyl isocyanate (MIC) and 336 g (2.0 mols) of hexamethylene diisocyanate are introduced into a flask equipped with a stirrer and dephlegmator. At a temperature of the flask contents of from 35° to 40° C., a continuous air stream of about 200 liters/h is passed through the mixture of the carbamic acid chlorides and isocyanates at normal pressure by means of a submerged frit. The condensate which accumulates in the condenser of the dephlegmator over a period of 1 hour at −30° C. (75.2 g) is collected in the cooled distillation receiver and has the following composition:

74.05 g of MIC
1.15 g of CSC.

The carrier gas stream is continuously recirculated.

What is claimed is:

1. A process for the preparation of relatively low boiling monoisocyanates of the formula:

R—NCO from the corresponding carbamic acid chlorides corresponding to the following general formula:

R—NH—COCl in which R represents an aliphatic hydrocarbon radical having from 1 to 5 carbon atoms; comprising adding an at least equivalent quantity, based on the hydrogen chloride bound in the carbamic acid chloride, of relatively high boiling organic monoisocyanate or polyisocyanate whose boiling point is higher than the boiling point of the relatively low boiling monoisocyanate to be produced, to the carbamic acid chlorides, optionally dissolved in inert organic solvents, and distilling off the relatively low boiling monoisocyanate from the thus-obtained mixture, optionally together with the solvent.

2. The process of claim 1, wherein the relatively low boiling monoisocyanate is removed by distillation.

3. The process of claim 1, wherein the relatively low boiling monoisocyanate is removed by means of an inert gas stream.

4. The process of claim 1, wherein the relatively low boiling monoisocyanate is removed by heating and/or by applying a vacuum.

5. The process of claim 1, wherein the carbamic acid chloride is selected from the group consisting of methyl, ethyl, and isopropyl carbamic acid chloride.

6. The process of claim 1, wherein the relatively high boiling organic or polyisocyanate has a boiling point at least 100° C. above the boiling point of the relatively low boiling monoisocyanate to be produced.

7. The process of claim 1, wherein the quantitative ratios are selected in such a way that from 1 to 10 mols of isocyanate groups in the relatively high boiling isocyanate are present per mol of carbamic acid chloride.

8. The process of claim 1, wherein the relatively high boiling organic monoisocyanate or polyisocyanate is selected from the group consisting of tetramethylene diisocyanate, hexamethylene diisocyanate and 1-isocyanato-3,3,5-trimethyl-5-isocyanato methyl cyclohexane.

9. The process of claim 1, wherein said inert organic solvents have a boiling point above the boiling point of the monoisocyanate to be produced.

10. The process of claim 1, wherein R represents, an olefinically unsaturated or a chlorine substituted, aliphatic hydrocarbon radical having from 1 to 5 carbon atoms.

11. A process for the preparation of alkyl isocyanates of the formula:

R—NCO by dehydrochlorinating the corresponding carbamic acid chlorides of the formula:

R—NH—COCl wherein R is alkyl of 1 to 5 carbon atoms; comprising reacting the carbamic acid chlorides with a high-boiling organic monoisocyanate or diisocyanate whose boiling point is higher than the boiling point of the alkyl isocyanate to be produced and above the decomposition point of its corresponding carbamic acid chloride, and removing the resulting alkyl isocyanate from the reaction mixture.

* * * * *